(12) United States Patent
Zeiner et al.

(10) Patent No.: US 8,747,304 B2
(45) Date of Patent: Jun. 10, 2014

(54) ATTACHMENT APPARATUS FOR AN ENDOSCOPE

(75) Inventors: Mark S. Zeiner, Mason, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 2282 days.

(21) Appl. No.: 11/589,995

(22) Filed: Oct. 31, 2006

(65) Prior Publication Data

US 2008/0103357 A1 May 1, 2008

(51) Int. Cl.
*A61B 1/00* (2006.01)

(52) U.S. Cl.
USPC ............ 600/127; 600/104; 600/114; 600/129

(58) Field of Classification Search
USPC ......... 600/104, 106, 114, 107, 115, 120–125, 600/127–130; 128/200.26, 207.14
See application file for complete search history.

(56) References Cited

U.S. PATENT DOCUMENTS

| | | | |
|---|---|---|---|
| 5,334,167 A * | 8/1994 | Cocanower | 604/523 |
| 6,517,569 B2 * | 2/2003 | Mikus et al. | 623/1.11 |
| 7,604,627 B2 * | 10/2009 | Kojouri | 604/516 |
| 2001/0053909 A1 | 12/2001 | Nakada et al. | |
| 2002/0198506 A1 * | 12/2002 | Whalen et al. | 604/328 |
| 2003/0135091 A1 | 7/2003 | Nakazawa et al. | |
| 2004/0210110 A1 | 10/2004 | Nakao | |
| 2005/0234297 A1 | 10/2005 | Devierre et al. | |
| 2005/0288550 A1 | 12/2005 | Mathis | |

FOREIGN PATENT DOCUMENTS

| | | |
|---|---|---|
| EP | 1639936 | 3/2006 |
| GB | 2301348 | 12/1996 |
| JP | 2003102668 | 4/2003 |

* cited by examiner

*Primary Examiner* — Anhtuan T Nguyen
*Assistant Examiner* — Ryan Henderson
(74) *Attorney, Agent, or Firm* — Welsh Flaxman & Gitler LLC

(57) ABSTRACT

An endoscopic attachment apparatus for coupling an endoscope with an endoscopic instrument includes an attachment ring having a ring body with first and second apertures respectively shaped and dimensioned for the receipt of an endoscope and an endoscopic instrument. The attachment ring includes an annular body defining the first aperture and the annular body is provided with an endoscope release mechanism for facilitating release of the endoscope from the attachment ring.

19 Claims, 11 Drawing Sheets

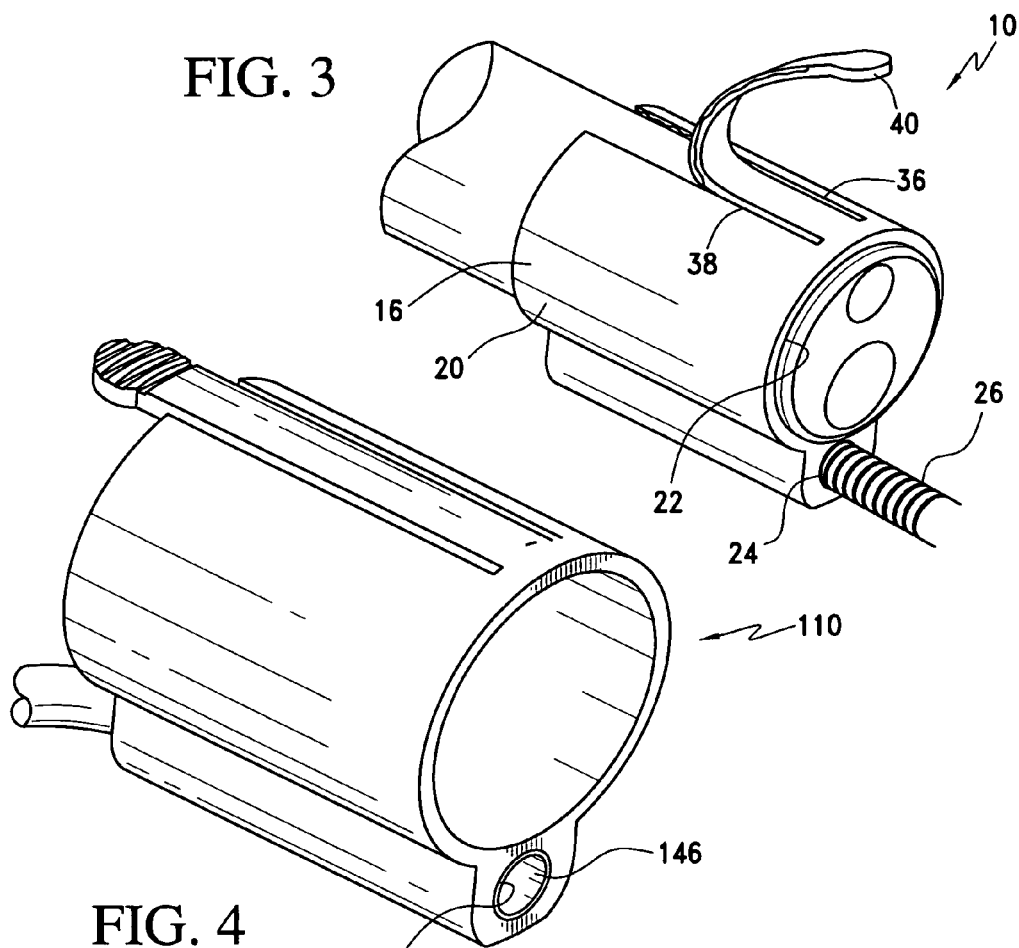
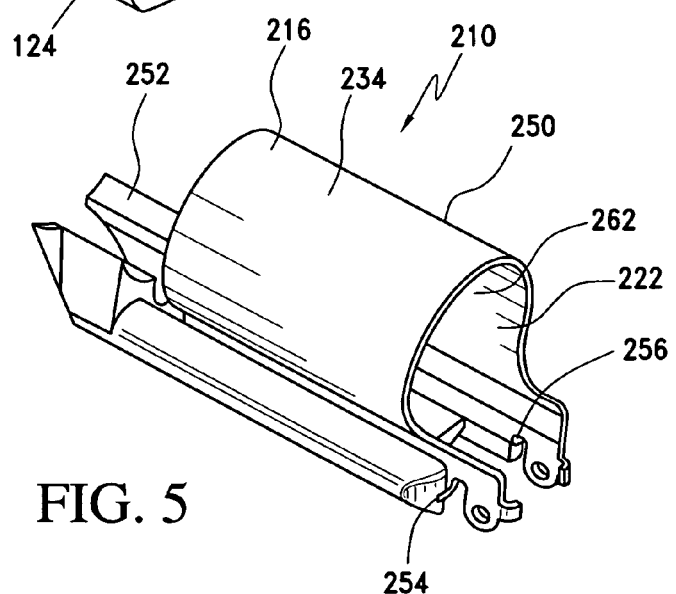

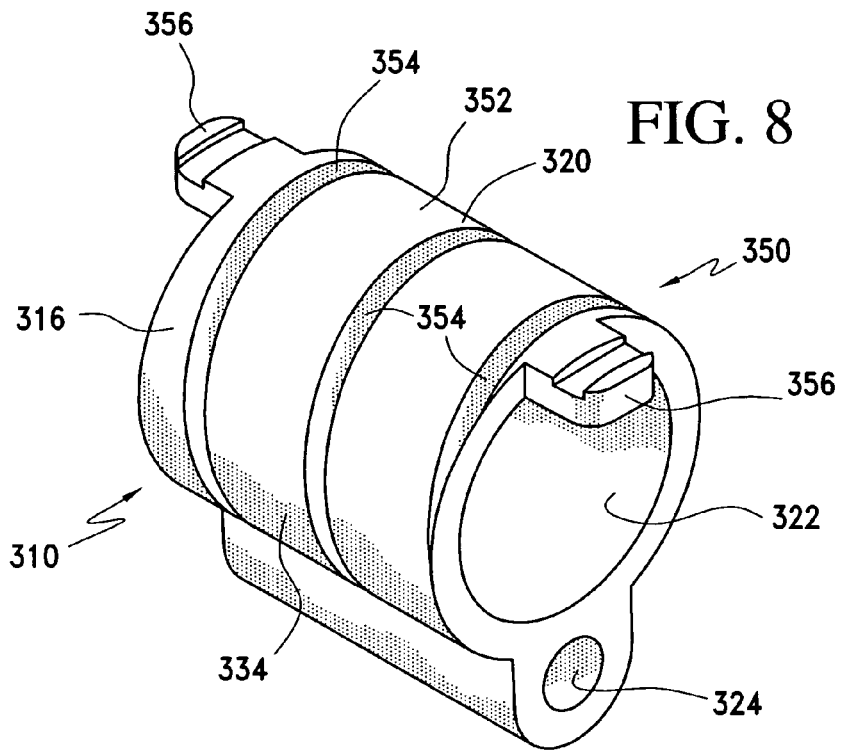
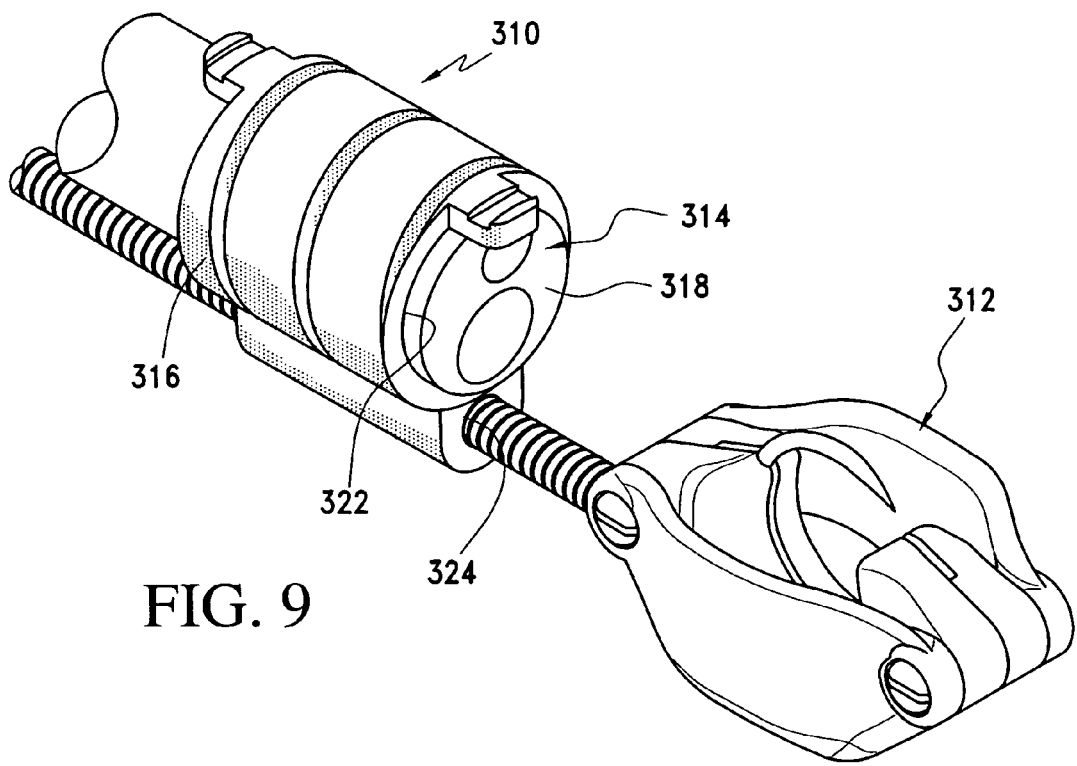

ATTACHMENT APPARATUS FOR AN ENDOSCOPE

BACKGROUND OF THE INVENTION

1. Field of the Invention

The invention relates to a surgical apparatus for instrument insertion. More particularly, the invention relates to an attachment apparatus for readily securing an endoscopic surgical instrument to an endoscope for insertion within a body cavity.

2. Description of the Prior Art

Endoscopic procedures have been rapidly developing over the past decade. These procedures often allow for the performance of surgical procedures with minimal trauma when compared to prior techniques requiring a large external opening to expose the internal organ or tissue requiring repair. In many instances, an endoscopic instrument is secured to the distal end of an endoscope for guiding the endoscopic instrument to the particular treatment site.

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" procedure employing an endoscope (often a rigid laparoscope). Laparoscopic procedures also commonly employ accessory devices that are inserted into a patient through trocars placed through the body wall.

Still less invasive treatments include those that are performed through insertion of an endoscope through a natural body orifice to a treatment site. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable section near the distal end that can be controlled by the user when utilizing controls at the proximal end.

Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 mm to 3.5 mm for the purpose of introducing and removing medical devices and other accessory devices to perform diagnosis or therapy within the patient. As a result, the accessory devices used by a physician can be limited in size by the diameter of the accessory channel of the scope used. Additionally, the physician may be limited to a single accessory device when using the standard endoscope having one working channel.

While certain specialized endoscopes having large working channel are known and other specialized endoscopes having two working channels are known, these large diameter/multiple working channel endoscopes can be relatively expensive and can have an outer diameter that makes the endoscope relatively stiff, or otherwise difficult to intubate. As such, systems have been developed whereby the endoscopic instrument is secured to the exterior of the endoscope, minimizing the need for endoscopes with large passageways.

These endoscopic instruments are currently secured to an endoscope through utilization of surgical tape or sutures wrapped about both the instrument and the endoscope in a manner holding them together. For example, U.S. Pat. Nos. 5,080,663, 6,869,395 and 6,997,931, as well as WO 0166018, disclose prior attachment structures.

As those skilled in the art will certainly appreciate, these structures are less than desirable. The tape is generally not sterile and is difficult to cut and apply in a sterile field. The tape is also difficult to remove and/or reapply in a different orientation. As to the use of sutures, they are also difficult to use in securing an endoscopic instrument to an endoscope.

Another attachment structure is disclosed in U.S. Patent Application Publication No. 2004/0230095 to Stefanchik. In accordance with this commonly owned patent application, a track structure is utilized in attaching an endoscopic instrument to an endoscope. Some other devices rely on a friction fit between the device and the endoscope. These may be difficult to remove after the procedure. Some of these friction fit devices are tight when applied to the endoscope and SURGILUBE, a lubricant made specifically for surgical procedures, is applied as a lubricant to ease assembly of the attachment means. However, as the device is used the SURGILUBE dries out and becomes like glue making the removal even more difficult.

With this in mind, a need exists for an improved mechanism for securing an endoscopic instrument to an endoscope. The present invention provides such an apparatus.

SUMMARY OF THE INVENTION

It is, therefore, an object of the present invention to provide an endoscopic attachment apparatus for coupling an endoscope with an endoscopic instrument. The apparatus includes an attachment ring having a ring body with first and second apertures respectively shaped and dimensioned for the receipt of an endoscope and an endoscopic instrument. The attachment ring includes an annular body defining the first aperture and the annular body is provided with an endoscope release mechanism for facilitating release of the endoscope from the attachment ring.

It is also an object of the present invention to provide an endoscopic attachment apparatus wherein the release mechanism includes a tear strip formed along the annular body.

It is also another object of the present invention to provide an endoscopic attachment apparatus wherein the tear strip includes first and second slots molded along the annular body.

It is also a further object of the present invention to provide an endoscopic attachment apparatus wherein the tear strip is provided with a tear tab at its free first end.

It is another object of the present invention to provide an endoscopic attachment apparatus including a tube installed in the second aperture, the tube extending proximally from the second aperture in a manner defining a passageway for the introduction of the endoscopic instrument to a surgical site without the removal of the endoscope.

It is still another object of the present invention to provide an endoscopic attachment apparatus wherein the release mechanism includes a helical tear away mechanism.

It is yet another object of the present invention to provide an endoscopic attachment apparatus wherein the helical tear away mechanism includes a helically oriented thick area and a helically oriented thin area oriented in a manner permitting ripping of the annular body.

It is a further object of the present invention to provide an endoscopic attachment apparatus wherein the helical tear away mechanism includes at least one tab secured to the thick area such that when the tab is pulled in a lateral manner the thin area is ripped such that a tear propagates from the tab helically along a longitudinal extent of the annular body.

It is still a further object of the present invention to provide an endoscopic attachment apparatus wherein the release mechanism includes a series of tear strips defined by radically oriented thick areas and thin areas.

It is yet a further object of the present invention to provide an endoscopic attachment apparatus including tabs secured to the respective thick areas.

It is also an object of the present invention to provide an endoscopic attachment apparatus wherein the release mechanism includes an insert providing a guide for cutting of the annular body in a manner permitting release of the endoscope therefrom.

It is also another object of the present invention to provide an endoscopic attachment apparatus wherein the release mechanism includes an insert formed of a brittle material.

It is also a further object of the present invention to provide an endoscopic attachment apparatus wherein the insert forms part of the annular body permitting cracking of the insert for opening of the annular body.

It is another object of the present invention to provide an endoscopic attachment apparatus wherein the first aperture is shaped and dimensioned for frictional engagement with an outer surface of the endoscope in a manner preventing rotation of the attachment ring relative to the endoscope.

It is a further object of the present invention to provide an endoscopic attachment apparatus wherein the second aperture is slightly larger than a shaft of the endoscopic instrument in a manner permitting movement of the endoscopic instrument relative to the endoscope for improved access to tissue.

It is also a further object of the present invention to provide an endoscopic attachment apparatus wherein the ring body includes a first member and a second member defining the first aperture therebetween, wherein the first member and the second member are releasably secured in a manner defining the release mechanism permitting selective release of an endoscope from within the first aperture.

It is still a further object of the present invention to provide an endoscopic attachment apparatus wherein the first member is substantially cylindrical and includes first and second outwardly extending flanges at free edges thereof, the first and second outwardly extending flanges being shaped and dimensioned for engaging the second member in a manner securely attaching the present attachment apparatus about an endoscope.

It is yet a further object of the present invention to provide an endoscopic attachment apparatus wherein the second member is a substantially elongated member shaped and dimensioned for engagement with the first and second flanges of the first member in a manner connecting the first and second edges of the first member to close a central aperture defined thereby.

It is also an object of the present invention to provide an endoscopic attachment apparatus including an instrument ring defining the second aperture.

It is another object of the present invention to provide an endoscopic attachment apparatus wherein the instrument is pivotally secured to the first member allowing the instrument ring to pivot relative to the first aperture.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a perspective view of the endoscopic attachment apparatus shown in FIG. 1 with the tear strip drawn forward.

FIG. 4 is a perspective view of an endoscopic attachment apparatus in accordance with an alternate embodiment.

FIGS. 5, 6 and 7 respectively show yet another embodiment of an endoscopic attachment apparatus with an assembled apparatus without an endoscope, an exploded view and an assembled apparatus with an endoscope and endoscopic instrument attached thereto.

FIG. 8 is a perspective view of an endoscopic attachment apparatus in accordance with yet another embodiment.

FIG. 9 is a perspective view of the endoscopic apparatus shown in FIG. 8 with an endoscope and endoscopic instrument attached thereto.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various embodiments described herein, the present invention relates to an endoscopic attachment apparatus for coupling an endoscope with an endoscopic instrument. The attachment apparatus includes an attachment ring having a ring body with substantially parallel first and second apertures respectively shaped and dimensioned for the receipt of an endoscope and an endoscopic instrument. The attachment ring includes an annular body defining the first aperture. The annular body is provided with an endoscope release mechanism for facilitating release of the endoscope from the attachment ring.

Figure 1:
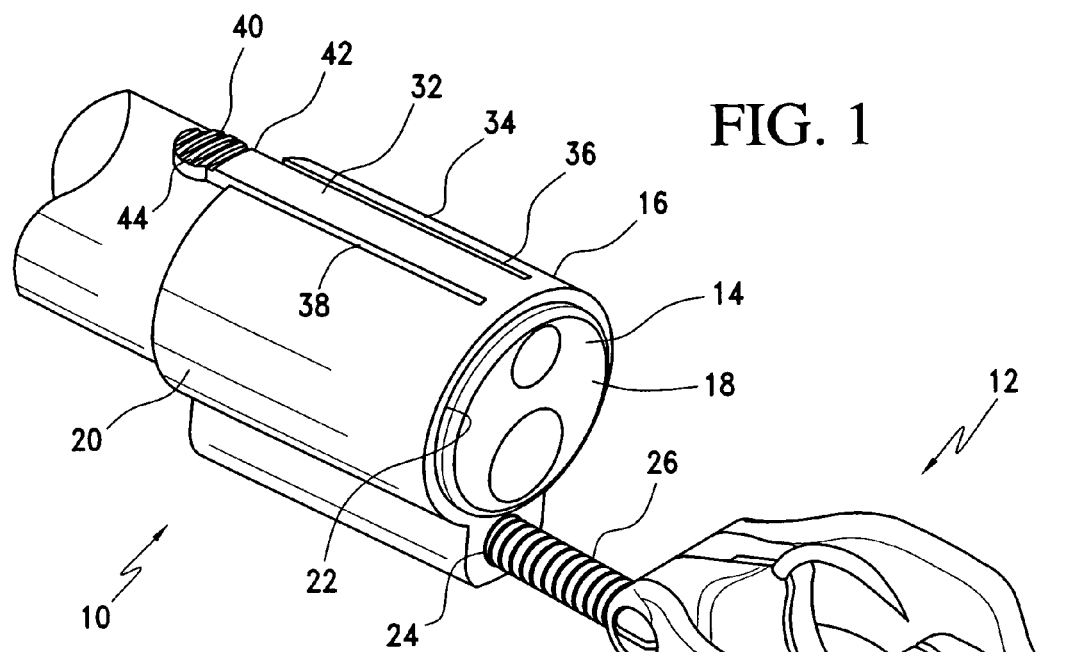
FIG. 1 is a perspective view of an endoscopic attachment apparatus in accordance with a preferred embodiment.
Figure 2:
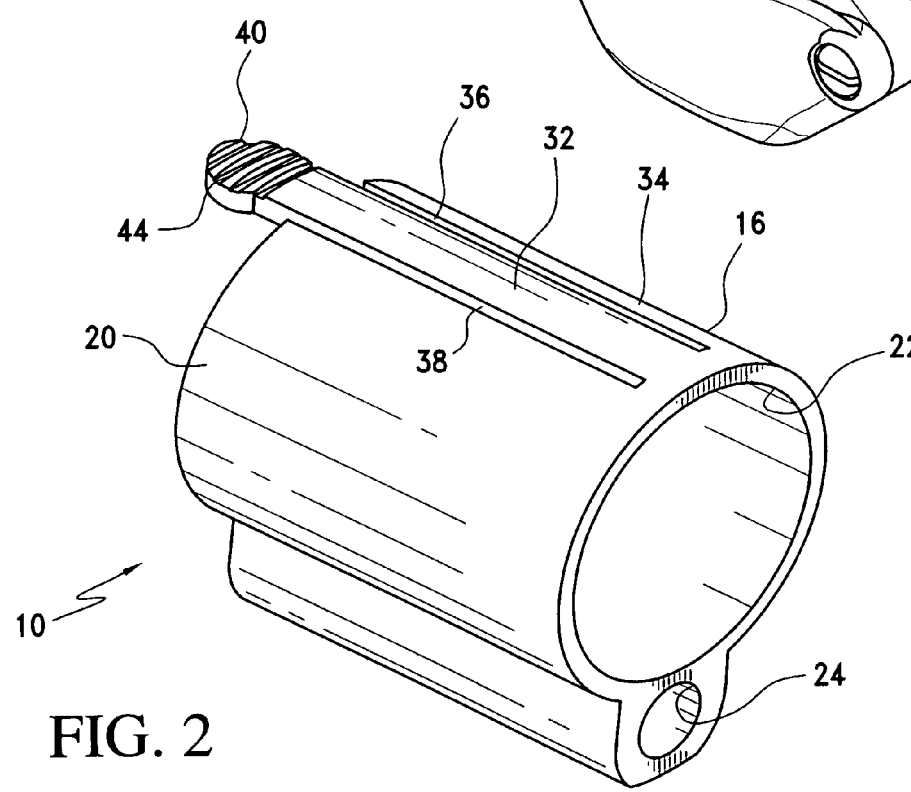
FIG. 2 is a perspective view of the endoscopic attachment apparatus shown in FIG. 1 with the endoscope and endoscopic instrument removed.

With reference to FIGS. 1, 2 and 3, a first embodiment of an endoscopic attachment apparatus 10 in accordance with the present invention is disclosed. The present attachment apparatus 10 is disclosed with reference to an endoscopic suturing apparatus 12 for the continuous application of a suture, although those skilled in the art will appreciate the attachment apparatus 10 may be used with a variety of endoscopic instruments without departing from the spirit of the present invention. The suturing apparatus 12 shown in accordance with a preferred embodiment of the present invention is disclosed in detail in U.S. patent application Ser. No. 11/394,174, entitled "METHOD FOR INSTRUMENT INSERTION THROUGH A BODY ORIFICE", filed Mar. 31, 2006, which is incorporated herein by reference. The present invention generally provides an attachment apparatus for attaching an endoscopic instrument to a flexible endoscope in a manner such that the endoscopic instrument is easily removable. The present attachment apparatus also ensures a single use thereof, thereby minimizing the potential for re-use of the attachment apparatus in a manner which could be potentially detrimental to a patient. Additionally, and as discussed below, the attachment apparatus may be designed with an adjustable size feature so that it can be adjusted in the operating room to fit the specific endoscope that is being used. This adjustable attachment apparatus eliminates the requirement of multiple attachment apparatuses being needed in the operating room and ensures that at least one is provided for fitting the endoscope to be used.

Improved functionality of the suturing apparatus 12 is achieved by the provision of the present attachment apparatus 10 specifically adapted for attaching the suturing apparatus 12, or other endoscopic instrument, to the distal end 18 of the endoscope 14, allowing for positioning of the endoscopic suturing apparatus 12 with respect to the endoscope 14.

The attachment apparatus 10 is composed of a scope attachment ring 16 which is secured about the distal end 18 of the endoscope 14 to which the endoscopic instrument 12 is to be mounted. The attachment ring 16 generally includes a ring body 20 having parallel first and second apertures 22, 24 respectively shaped and dimensioned for the receipt of the endoscope 14 and the support shaft 26 of the endoscopic instrument 12 secured to the endoscope 14. The first aperture 22 is shaped and dimensioned for frictional engagement with the outer surface of the endoscope 14 in a manner preventing rotation of the attachment ring 16 relative to the endoscope 14. In accordance with a preferred embodiment, the attachment ring 16 is molded from a resilient material adapted to fit over the endoscope 14 in a manner creating a frictional engagement. For example, it is contemplated the attachment ring may be molded from various resilient materials, such as, ADIPRENE, SANTOPRENE, silicone, urethane, etc.

The second aperture 24 is shaped and dimensioned for receiving the shaft 26 of the endoscopic instrument 12 and, in accordance with a preferred embodiment thereof, the second aperture 24 is slightly larger than the shaft 26 of the endoscopic instrument 12. In this way, the endoscopic instrument 12 may be rotated relative to the endoscope 14 for improved access to tissue.

The attachment ring 16 is provided with a tear strip 32 along the first aperture 22, the tear strip 32 functioning as a release mechanism facilitating release of the endoscope 14 from the attachment ring 16. The tear strip 32 allows for ready detachment of the attachment ring 16 from the endoscope 14 for separation of the endoscope 14 from the endoscopic instrument 12 secured thereto. The use of a tear strip 32 in accordance with the present invention further prevents re-use of the attachment ring 16 after its initial use due to the destructive nature of the tear strip 32.

More particularly, the attachment ring 16 includes an annular body 34 defining the first aperture 22. The annular body 34 includes parallel slots 36, 38 molded along the annular body 34. The parallel slots 36, 38 are composed of thin areas extending along the length of the annular body 34 in a manner creating weakened sections for detachment of the tear strip 32. The parallel slots 36, 38 define the edges of the tear strip 32 that is integrally formed as part of the annular body 34.

The tear strip 32 is further provided with a tear tab 40 at its free first end 42. The tear tab 40 includes knurled sections 44. The knurled sections 44 allow for easy gripping either manually or with surgical tools.

In practice, one grips the tear tab 40 and pulls the tear strip 32 upwardly away from the endoscope 14 and toward the second end 44 of the tear strip 32 while twisting back and forth to weaken the thin parallel slots 36, 38. This is preferably done with surgical tools (e.g., forceps, Babcock's) and a twisting motion. As the parallel slots 36, 38 break along the annular body 34, the tear strip 32 is detached from the annular body 34. The application of upward and rearward motion (and/or twisting motion) is continued until the second end 44 of the tear strip 32 is detached from the annular ring 16, thereby opening the annular ring 16 for removal of the endoscope 14 therefrom.

Referring to FIG. 4, and in accordance with an alternate embodiment, the attachment apparatus 110 includes a tube 146 which may be installed in the second aperture 124 so as to extend proximally from the second aperture 124 in a manner defining a passageway for the endoscopic instrument 12 to the surgical site without removal of the endoscope 14. The installation of a tube 146 in this manner allows endoscopic instruments to be introduced into the surgical site without the removal of the endoscope. The tube 146 functions as a delivery tube where the surgical instrument is selectively inserted through the proximal end of the tube and delivered to the distal end, surgical site. This effectively creates a secondary passageway through which a surgical instrument may be passed for accessing a surgical site.

Figure 6:
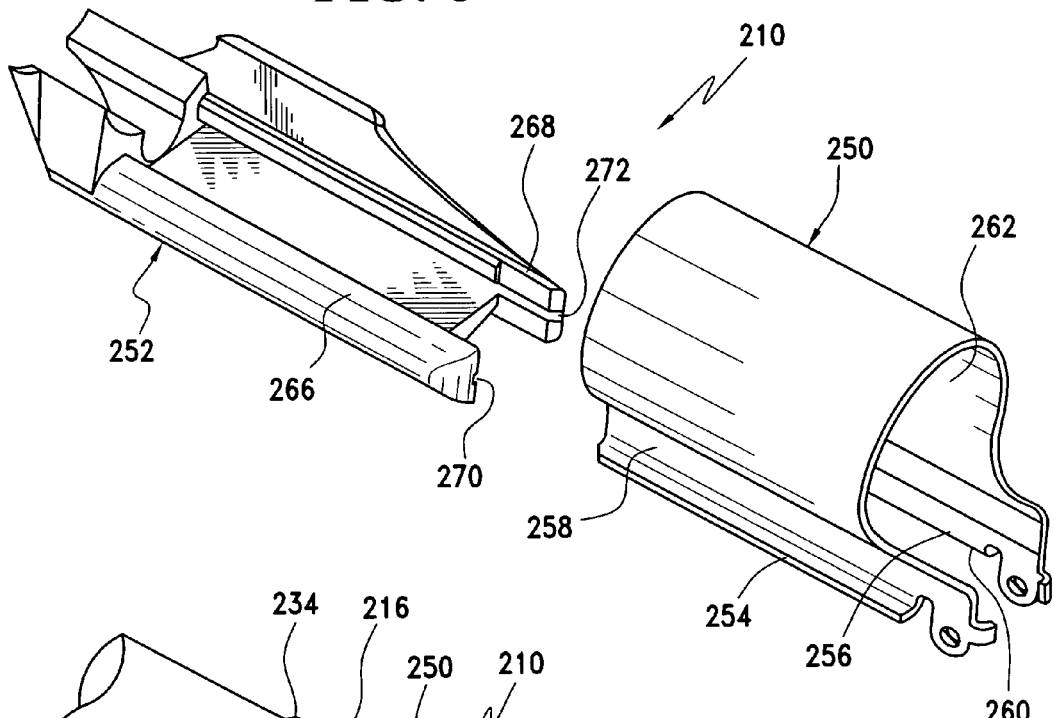
Figure 7:
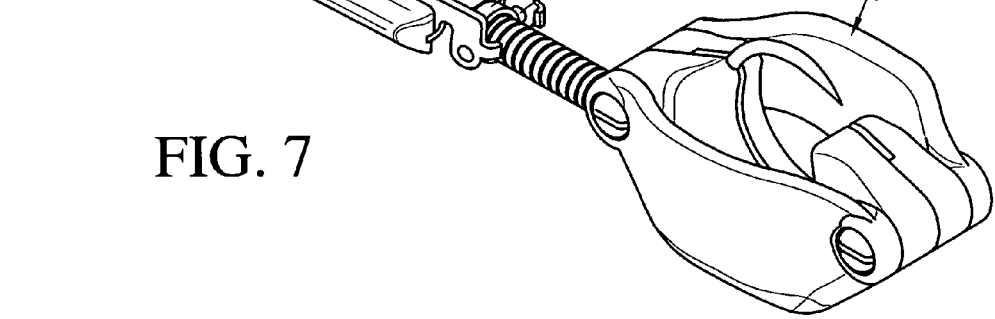

With reference to FIGS. 5, 6 and 7, an alternate endoscopic attachment apparatus 210 is disclosed. As with the prior embodiments, the attachment apparatus 210 includes a ring body 216 having substantially parallel first and second apertures 222, 224 respectively shaped and dimensioned for the receipt of an endoscope 214 and an endoscopic instrument 212. The attachment ring 216 includes an annular body 234 defining the first aperture 222. The annular body 234 is provided with an endoscope release mechanism for facilitating release of the endoscope 214 from the attachment ring 216.

The attachment apparatus 210 achieves release, that is, provides a release mechanism, of the endoscope 214 from the annular body 234 through the provision of a first member 250 and a second member 252 defining the first aperture 222 therebetween, wherein the first member 250 and the second member 252 are releasably secured in a manner permitting selective release of an endoscope 214 from within the first aperture 222.

In accordance with a preferred embodiment, the first member 250 is shaped and dimensioned to wrap about the endoscope 214. The first member 250 is substantially cylindrical and includes first and second outwardly extending flanges 254, 256 at the free edges 258, 260 thereof. As will be described below in greater detail, the first and second outwardly extending flanges 254, 256 are shaped and dimensioned for engaging the second member 252 in a manner securely and selectively attaching the present attachment apparatus 210 about an endoscope 214. In accordance with a preferred embodiment, the first member is composed of stainless steel having a thickness of the approximately 0.020 inches. It is further contemplated that a thin rubber material can be attached to the inner diameter of the first aperture 222 so as to provide a cushion for preventing damage to the endoscope tip. The tip of the endoscope is soft and flexible and care should be taken to not let the attachment apparatus damage the endoscope. The thin rubber material could also be used as a size adjustability feature to allow attachment to different size scopes.

The second member 252 is a substantially elongated member shaped and dimensioned for engagement with the first and second flanges 254, 256 of the first member 250 in a manner connecting the first and second edges 258, 260 of the first member 250 to close the central first aperture 222 defined thereby. With this in mind, the second member 252 includes a substantially flat base 264 having a first edge 266 and a second edge 268. The first and second edges 266, 268 are respectively provided with inwardly directed recesses 270, 272 shaped and dimensioned for receipt of the first and second flanges 254, 256 extending from the first and second edges 258, 260 of the first member 250. As such, the second member 252 may be slid over the first and second flanges 254, 256 of the first member 250 with the first and second flanges 254, 256 seating within the first and second recesses 270, 272 of the second member 252.

The first and second recesses 270, 272 and the first and second flanges 254, 256 are shaped and dimensioned to provide for a frictional engagement therebetween in a manner selectively locking the first and second members 250, 252 relative to each other with the endoscope 214 held therebetween. In addition, the first aperture 222 defined by the first and second members 250, 252 is shaped and dimensioned to snuggly receive the endoscope 214 in a manner creating additional frictional resistance holding the endoscope 214 therebetween.

The attachment apparatus 210 as shown in FIG. 7 further includes an instrument ring 274 defining the second aperture 224. The instrument ring 274 is pivotally secured to the distal end of the first member 250 in a manner allowing the instrument ring 274, and, therefore, the endoscopic instrument 212, to pivot relative to the endoscope 214. As with the prior embodiments, the instrument ring 274 is made from a bearing material (that is, a generally low friction material allowing the movement of the endoscopic instrument relative thereto) shaped and dimensioned for positioning about the shaft of endoscopic instrument 212. More particularly, the instrument ring 274 is basically a bushing with a shaft inside. As a result, the shaft of a surgical instrument 212 inserted therein can rotate within the bushing and relative to the endoscope 214. With this in mind, the instrument ring 274 is constructed from various known materials well suited for this purpose.

Figure 10:
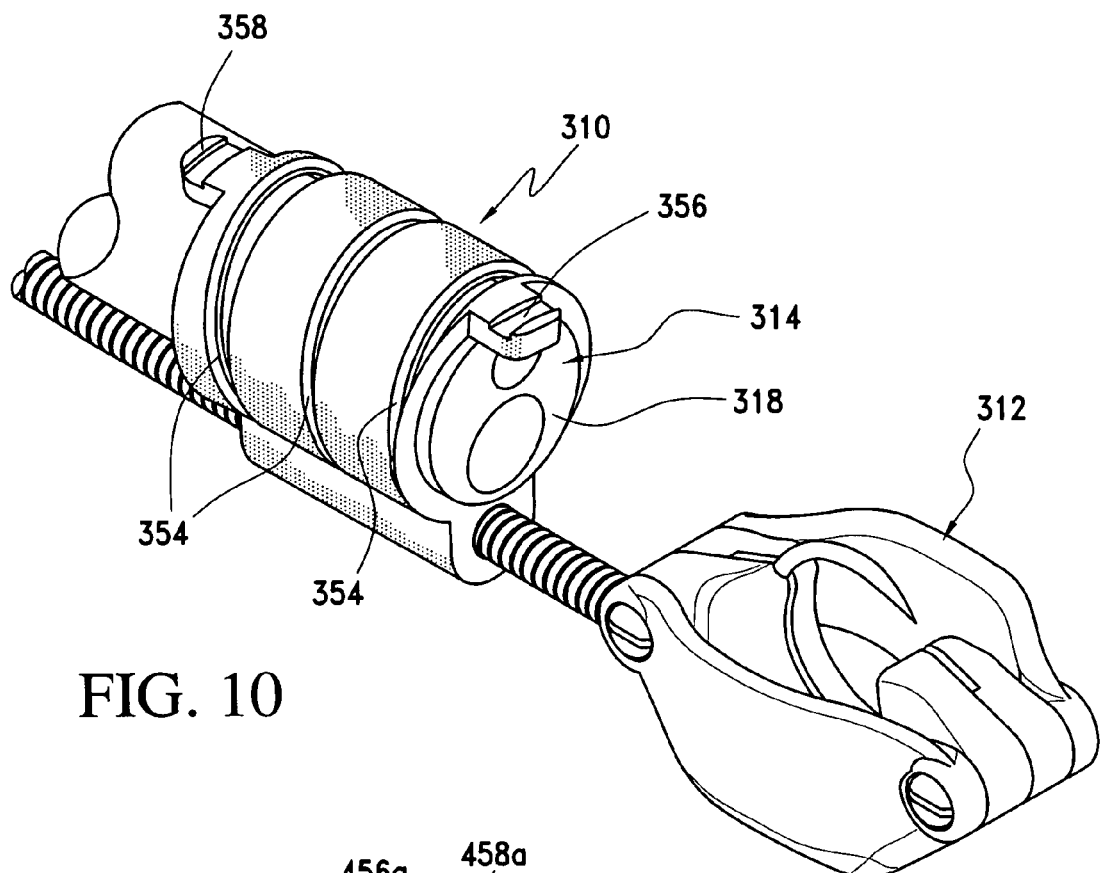
FIG. 10 is a perspective view of the endoscopic apparatus shown in FIG. 8 with the tear away mechanism released.

Referring to FIGS. 8, 9 and 10, yet another embodiment of an endoscopic attachment apparatus 310 in accordance with the present invention is disclosed. The attachment apparatus 310 is composed of a scope attachment ring 316 which is secured about the distal end 318 of the endoscope 314 to which the endoscopic instrument 312 is to be mounted. The scope attachment ring 316 generally includes a ring body 320 having parallel first and second apertures 322, 324 respectively shaped and dimensioned for receipt of the endoscope 314 and the support shaft 326 of an endoscopic instrument 312 secured to the endoscope 314. The first aperture 322 is shaped and dimensioned for frictional engagement with the outer surface of the endoscope 314 in a manner preventing rotation of the scope attachment ring 316 relative to the endoscope 314. As with the prior embodiment disclosed with reference to FIGS. 1 and 2, the scope attachment ring 316 is molded from a resilient material adapted to fit over the endoscope 314 in a matter creating a frictional engagement. The second aperture 324 is shaped and dimensioned for receiving the shaft 326 of the endoscopic instrument 312 and, in accordance with the preferred embodiment thereof, the second aperture 324 is slightly larger than the shaft 326 of the endoscopic instrument 312. In this way, the endoscopic instrument 312 may be rotated relative to the endoscope 314 for improved access to the tissue.

In accordance with a preferred embodiment, the attachment ring 316 is provided with a helical tear away mechanism 350, the tear away mechanism 350 functioning as a release mechanism facilitating release of the endoscope 314 from the attachment ring 316. The tear away mechanism 350 allows for ready detachment of the attachment ring 316 from the endoscope 314 for separation of the endoscope 314 from the endoscopic instrument 312 secured thereto. The use of a helical tear away mechanism 350 in accordance with the present invention further prevents reuse of the attachment ring 316 after its initial use due to the destructive nature of the tear away mechanism 350.

More particularly, the attachment ring 316 includes an annular body 334 defining the first aperture 322. The annular body 334 includes a helically oriented thick area 352 and a helically oriented thin area 354 positioned such that when the medical practitioner pulls on either of first or second tabs 356, 358 secured to opposite ends of the annular body 334 in a lateral manner, the thin area 354 is ripped in a manner such that the tearing of the annular body 334 propagates from the tab 356, 358 helically along the longitudinal extent of the annular body 334. Once this has been done, the endoscope 312 may be freely removed from the attachment apparatus 310 allowing for separation of the surgical instrument 312 and the end of the endoscope 314.

Figure 11:
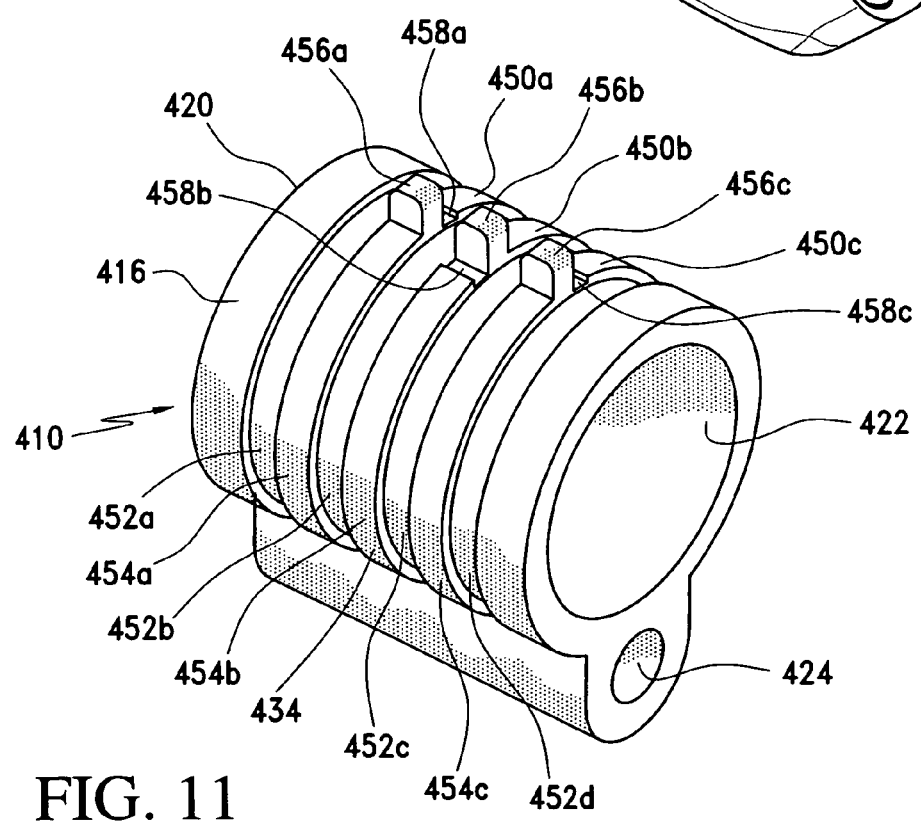
FIG. 11 is a perspective view of an endoscopic attachment apparatus in accordance with a further embodiment.
Figure 12:
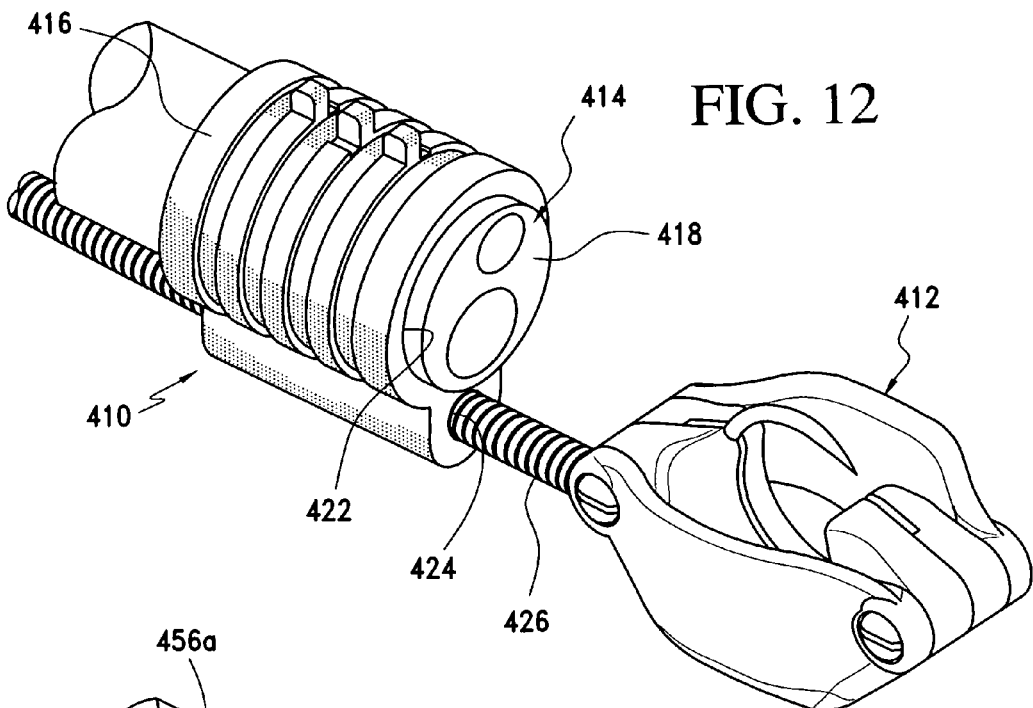
FIG. 12 is a perspective view of the endoscopic attachment apparatus shown in FIG. 11 with an endoscope and endoscopic instrument attached thereto.
Figure 13:
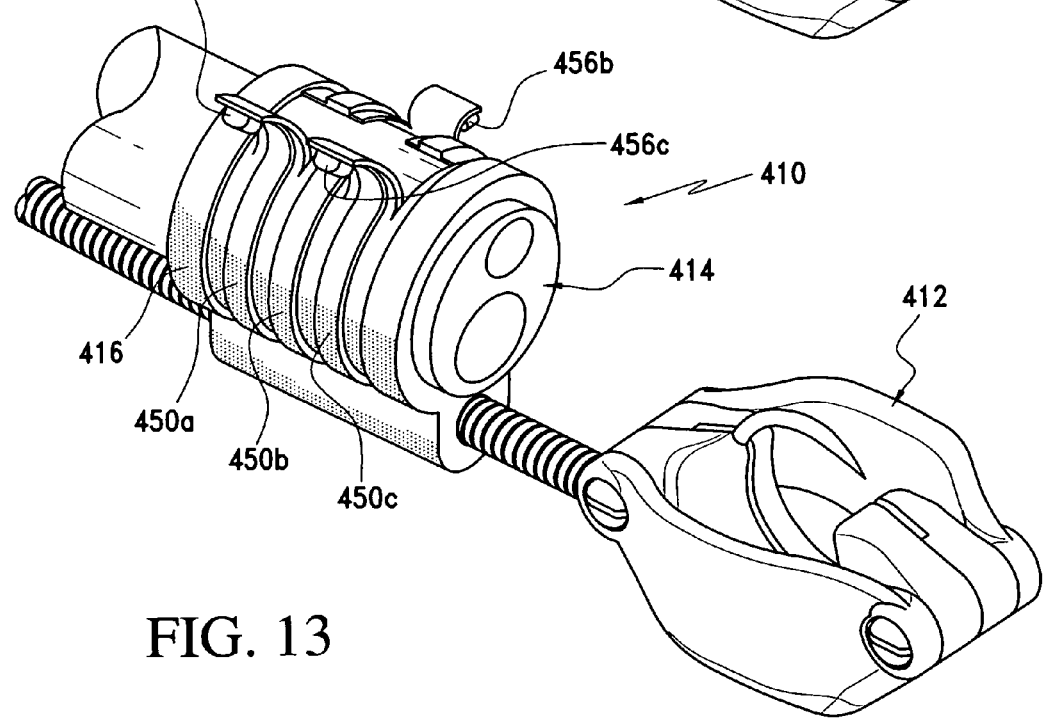
FIG. 13 is a perspective view of the endoscopic attachment apparatus shown in FIG. 11 with the tear strips actuated.

With reference to FIGS. 11, 12 and 13, and in accordance with another embodiment, the attachment apparatus 410 is also composed of an endoscope attachment ring 416 which is secured about the distal end 418 of the endoscope 414 to which the endoscopic instrument 412 is to be mounted. The attachment ring 416 generally includes a ring body 420 having parallel first and second apertures 422, 424 respectively shaped and dimensioned for the receipt of the endoscope 414 and the support shaft 426 of an endoscopic instrument 412 secured to the endoscope 414. With regard to the endoscope 414, the first aperture 422 is shaped and dimensioned for frictional engagement with the outer surface of the endoscope 414 in a manner preventing rotation of the attachment ring 416 relative to the endoscope 414. In accordance with a preferred embodiment, and as discussed above with regard to the prior embodiments, the attachment ring 416 is molded from a resilient material adapted to fit over the endoscope 414 in a manner creating a frictional engagement.

The second aperture 424 is shaped and dimensioned for receiving the shaft 426 of the endoscopic instrument 412 and, in accordance with a preferred embodiment thereof, the second aperture 424 is slightly larger than the shaft 426 of the endoscopic instrument 412. In this way, the endoscopic instrument 412 may be rotated relative to the endoscope 414 for improved access to tissue.

The attachment ring 416 is provided with a series of radially oriented tear strips 450a-c allowing for ready detachment of the attachment ring 416 from the endoscope 414 for separation of the endoscope 414 from the endoscopic instrument 412 secured thereto. Although three tear strips are disclosed in accordance with a preferred embodiment of the present invention, those skilled in the art will appreciate that greater or fewer tear strips may be used without departing from the spirit of the present invention. The tear strips 450a-c function as a release mechanism facilitating release of the endoscope 414 from the attachment ring 416. More particularly, the attachment ring 416 includes an annular body 434 defining the first aperture 422. The annular body 434 includes a series of parallel slots 452a-d extending radially about the annular body 434. The slots, or thin areas, 452a-d are separated by respective first, second and third thick sections 454a-c to which first, second and third tear tabs 456a-c respectively are secured. In practice, the tabs 456a-c are pulled or twisted with forceps, or other common surgical tool, to rip the thin areas 452a-d adjacent thereto and thereby reduce the frictional holding force of the attachment. Once this has been done, the endoscope 414 maybe freely removed from the attachment apparatus 410 allowing separation of the surgical instrument 412 and the endoscope 414. Improved control of the tearing is achieved by positioning a thin section 458a-c across the respective thick sections 454a-c adjacent the tabs 456a-c.

Figure 14:
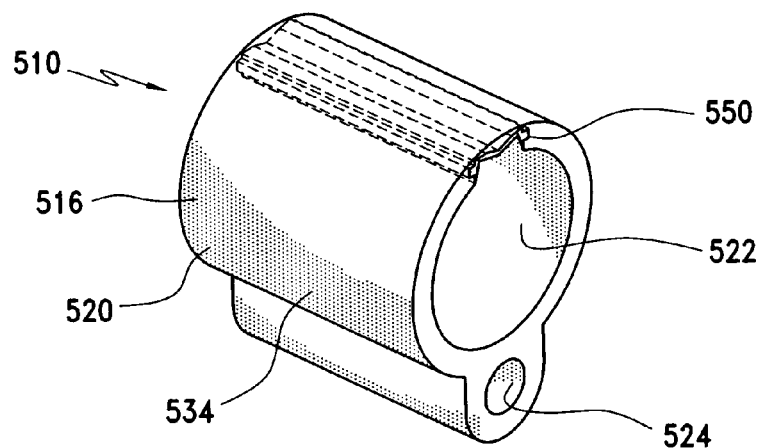
FIG. 14 is a perspective view of an endoscopic attachment apparatus in accordance with still another embodiment.
Figure 15:
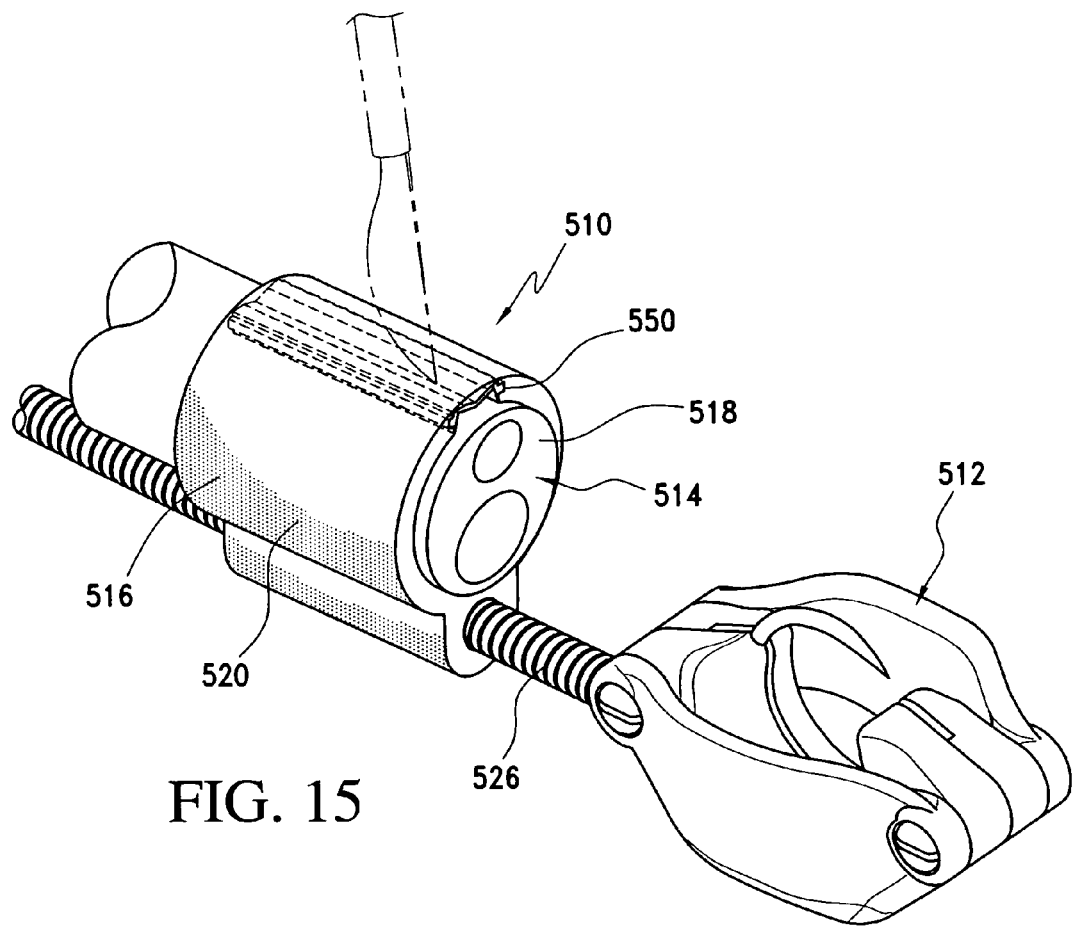
FIG. 15 is a perspective view of the endoscopic attachment apparatus shown in FIG. 14 with an endoscope and endoscopic instrument attached thereto. This figure also shows the utilization of a knife to cut the endoscopic attachment apparatus for release of the endoscope.
Figure 16:
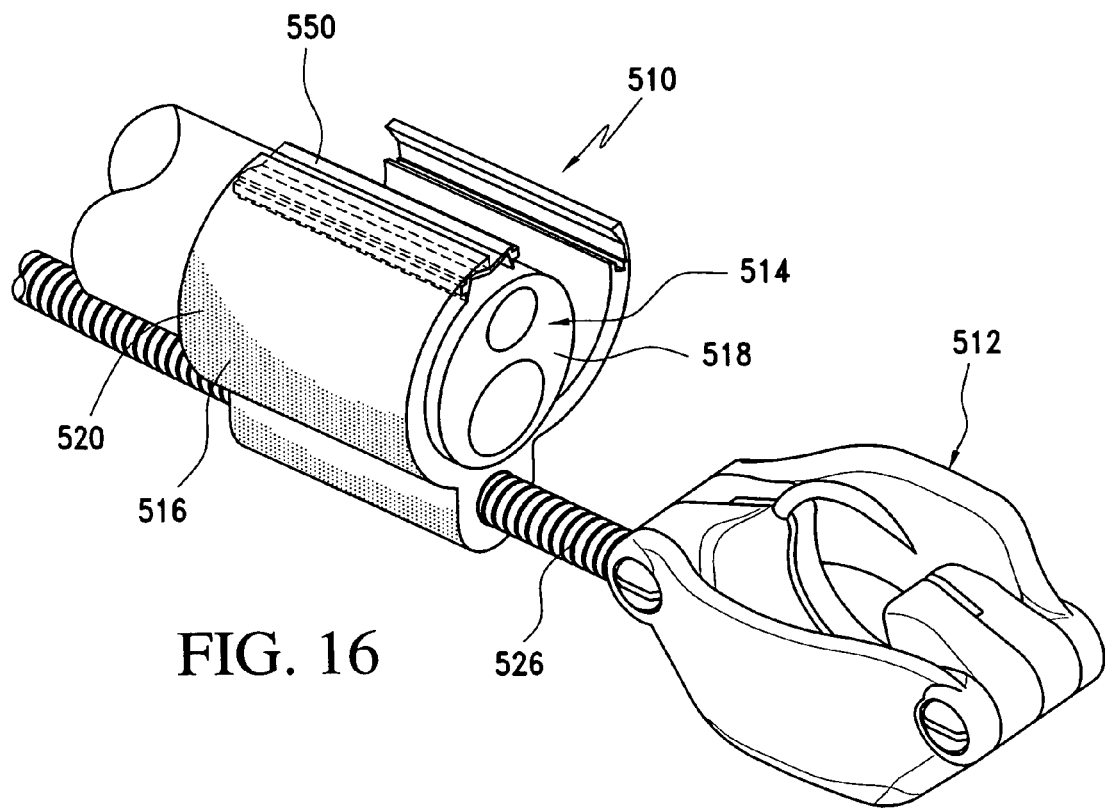
FIG. 16 is a perspective view of the endoscopic attachment apparatus shown in FIG. 14 with the attachment ring opened in accordance with the present invention.

With reference to FIGS. 14, 15 and 16, and in accordance with yet another embodiment, the attachment apparatus is composed of a scope attachment ring 516 which is secured about the distal end 518 of the endoscope 514 to which the endoscopic instrument 512 is to be mounted. The attachment ring 516 generally includes a ring body 520 having parallel first and second apertures 522, 524 respectively shaped and dimensioned for receipt of the endoscope 514 and the support shaft 526 of an endoscopic instrument 512 secured to the endoscope 514. With regard to the endoscope 514, the first aperture 522 is shaped for frictional engagement with the outer surface thereof in a manner preventing rotation of the attachment ring 516 relative to the endoscope 514. The second aperture 524 is shaped and dimensioned for receiving the shaft 526 of the endoscopic instrument 512 and, in accordance with a preferred embodiment, the second aperture 524 is slightly larger than the shaft 526 of the endoscopic instrument 512. In this way, the endoscopic instrument 512 may be rotated relative to the endoscope 514 for improved access to tissue.

As with the prior embodiments, the attachment ring 516 is molded from a resilient material adapted to fit over the endoscope 514 in a manner creating a frictional engagement. The attachment ring 516 includes an annular body 534 defining the first aperture 522. Within the annular body 534 is positioned a metal, cut resistant insert 550, the metal insert 550 facilitating cutting of the annular body 534 and thereby functioning as a release mechanism facilitating released of the endoscope 514 from the attachment ring 516. The metal, cut resistant insert 550 allows one to use a scalpel to cut through the rubber compound of the annular body 534 and permit release of the endoscope 514 therefrom. Once the annular body 534 is cut down to the insert 550, all the hoop stresses of the annular body 534 are lost and the strength of the attachment apparatus 510 is much reduced in a manner allowing one to readily remove the endoscope 514 therefrom. The metal, cut resistant insert 550 prevents the endoscope 514 from being damaged by a scalpel during cutting.

Figure 17:
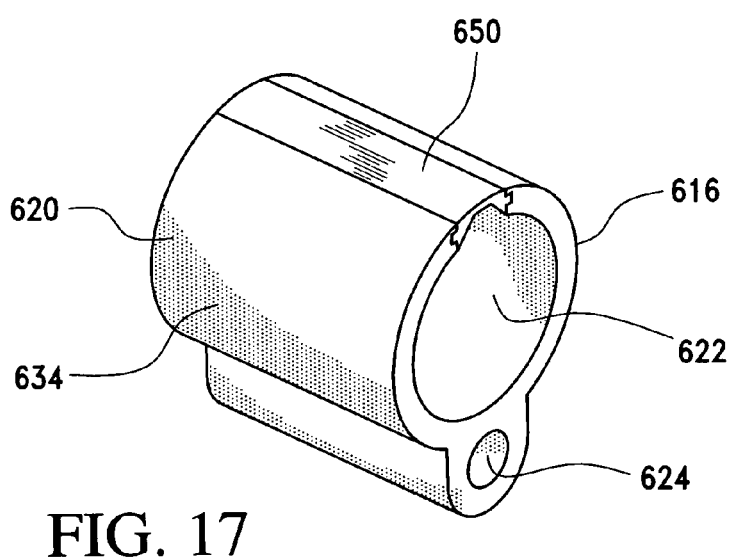
FIG. 17 is a perspective view of an endoscopic attachment apparatus in accordance with still a further embodiment of the present invention.
Figure 18:
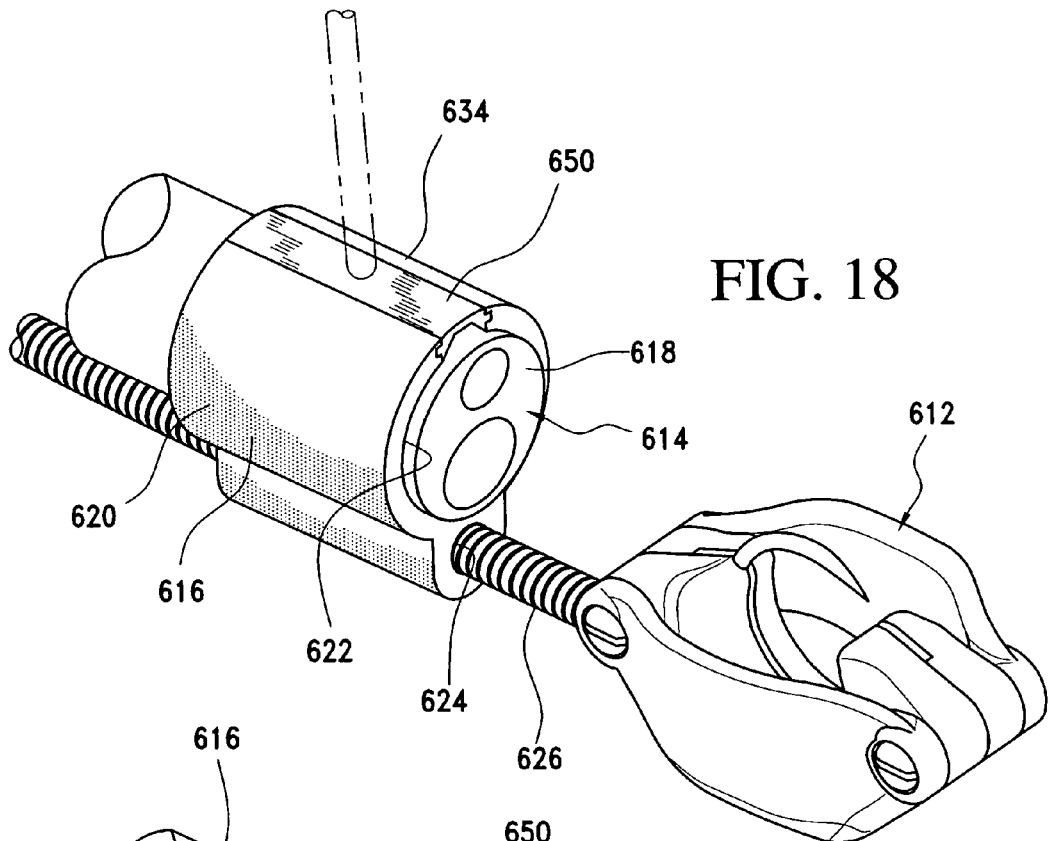
FIG. 18 is a perspective view of the endoscopic attachment apparatus shown in FIG. 17 with an endoscope and endoscopic instrument attached thereto. This figure further shows the application of pressure to an insert for opening of the endoscopic attachment apparatus.
Figure 19:
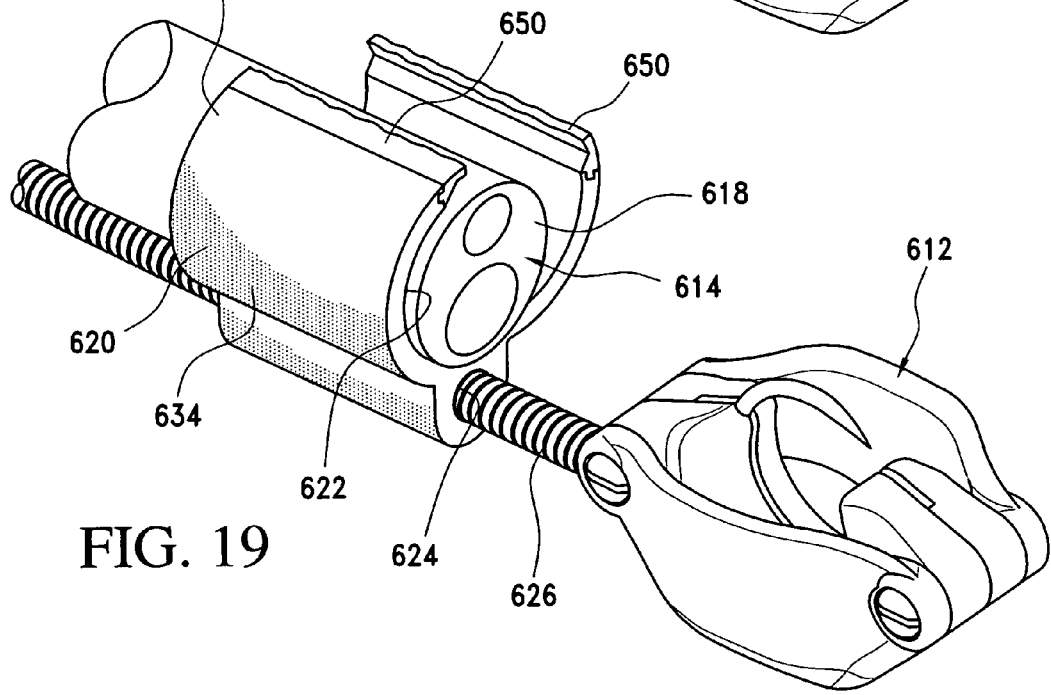
FIG. 19 is a perspective view of the apparatus as shown in FIG. 17 showing the insert cracked open and the endoscope ready for removal.
Figure 20:
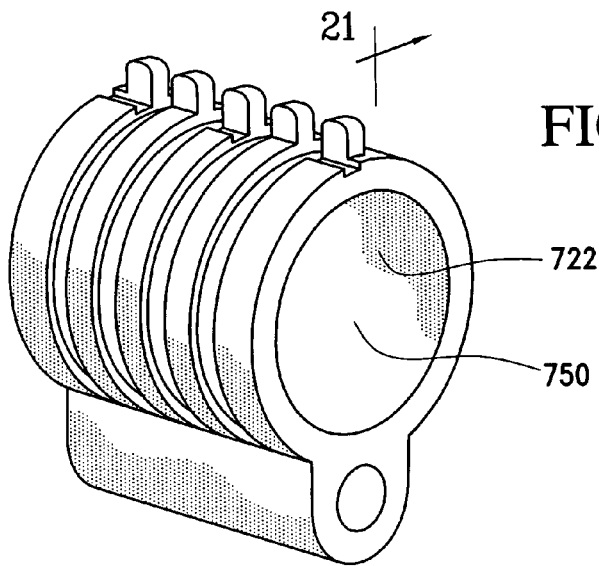
FIGS. 20, 21, 22, 23, 24 and 25 are various views showing an endoscopic attachment apparatus, similar to that disclosed in FIGS. 11, 12 and 13, wherein the inner surface is tapered for accommodating endoscopes of various diameters.
Figure 21:
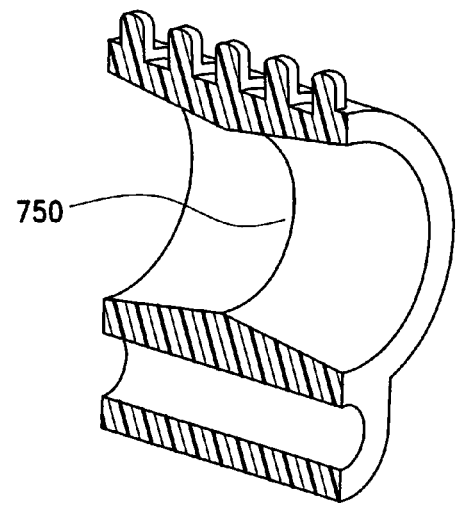
Figure 22:
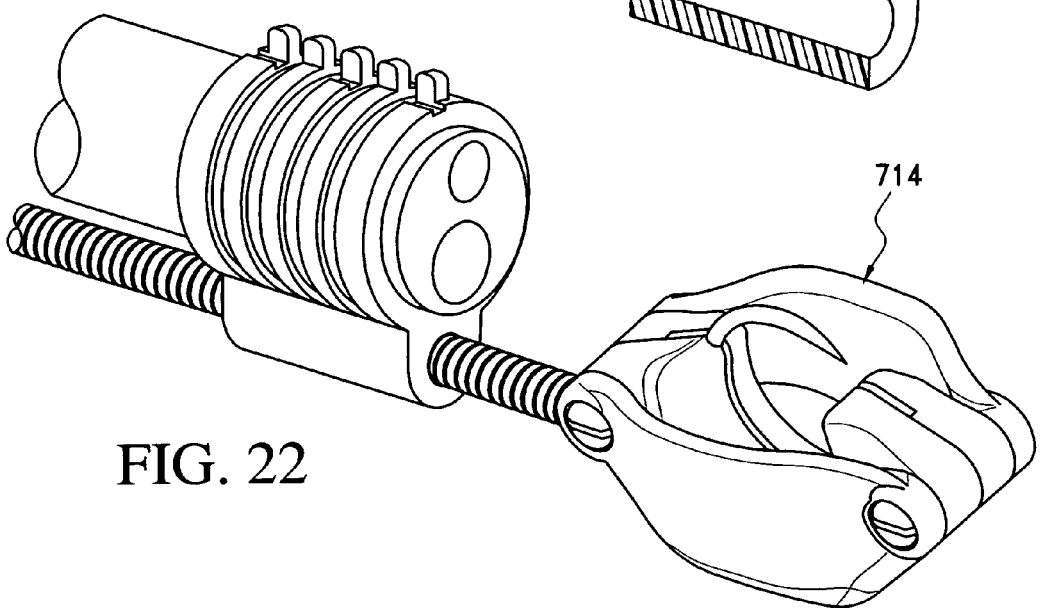
Figure 23:
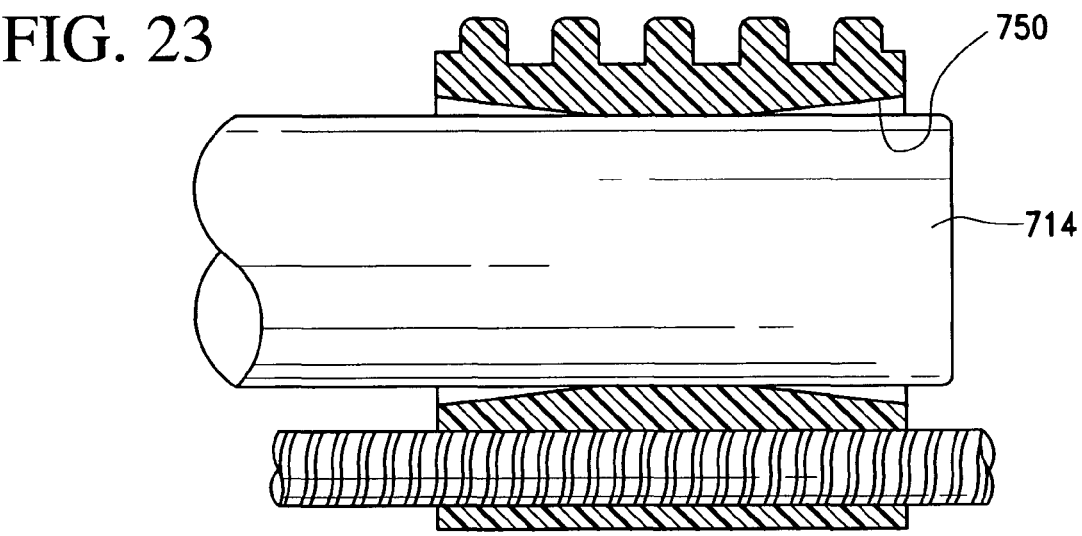
Figure 24:
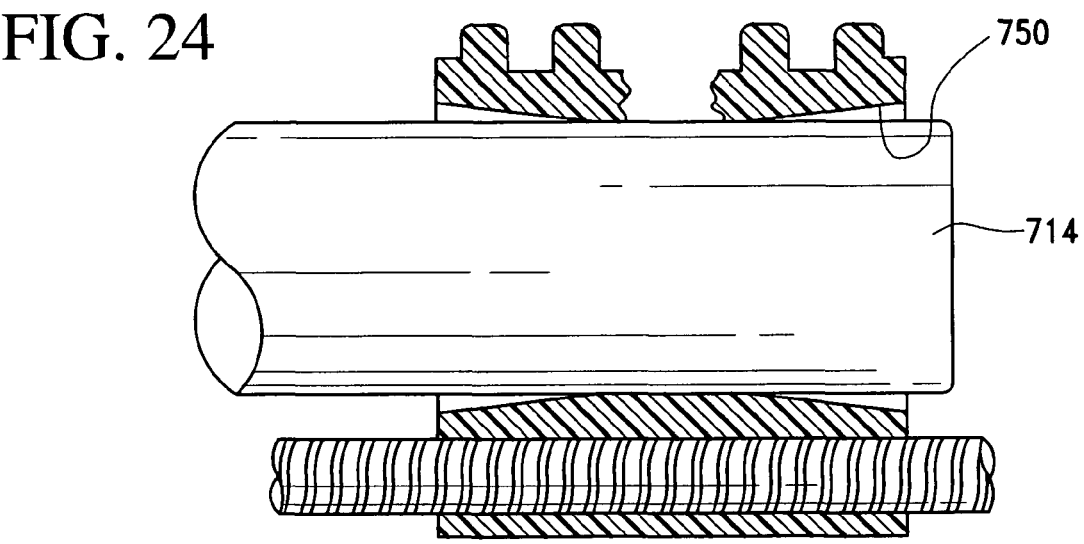
Figure 25:
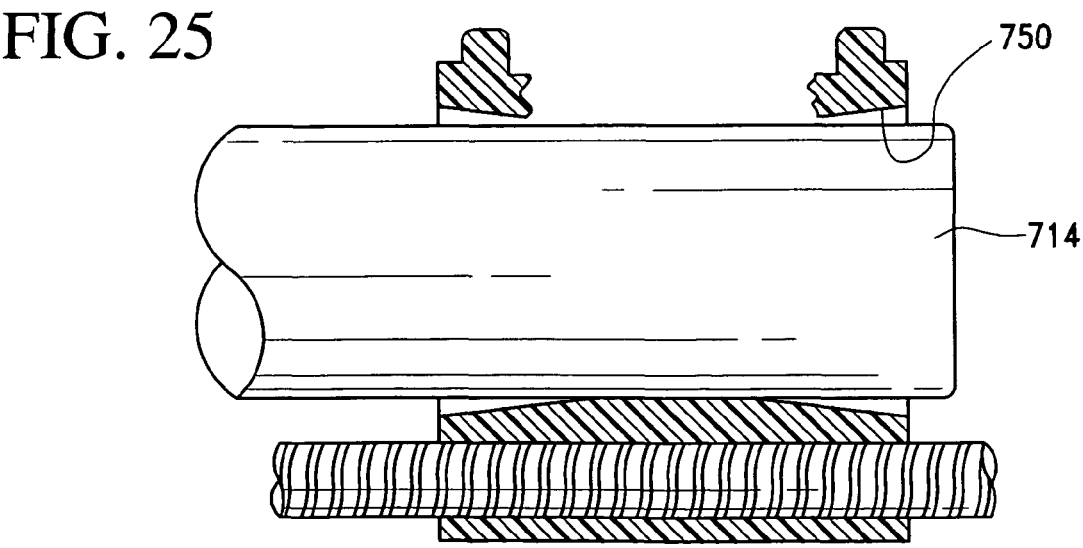

In accordance with still a further embodiment, and with reference to FIGS. 17, 18 and 19, the attachment apparatus is composed of a scope attachment ring 616 which is secured about the distal end 618 of the endoscope 614 to which the endoscopic instrument 612 is to be mounted. The attachment ring 614 generally includes a ring body 620 having parallel first and second apertures 622, 624 respectively shaped for receipt of the endoscope 614 and the support shaft 626 of an endoscopic instrument 612 secured to the endoscope 614. With regard to the endoscope 614, the first aperture 622 is shaped for frictional engagement with the outer surface thereof in a manner preventing rotation of the attachment ring 616 relative to the endoscope 614. The second aperture 624 is shaped and dimensioned for receiving the shaft 626 of the endoscopic instrument 612 and, in accordance with a preferred embodiment, the second aperture 624 is slightly larger than the shaft 626 of the endoscopic instrument 612. In this way, the endoscopic instrument 612 may be rotated relative to the endoscope 614 for improved access to tissue.

The attachment ring 616 is substantially molded from a resilient material adapted to fit over the endoscope 614 in a manner creating a frictional engagement. However, the attachment ring 616, and, in particular an annular body 634 defining the first aperture 622, includes an insert 650 composed of a brittle material along a portion of the ring defined thereby. In this way, the annular body 634 defining the first aperture 622 has a composite construction. The use of a brittle insert 650 along the annular body 634 results in a component which is strong enough to hold up to use, but will crack when pressure is applied directly thereto. As such, one may open the annular body 634 by simply applying pressure in a manner cracking the brittle insert 650 and thereby opening the entire assembly to permit the free retrieval of the endoscope 614.

Regardless of which of the embodiments described above is employed, the first aperture may be shaped and dimensioned to permit utilization with endoscopes of various diameters. In particular, and with reference to FIGS. 20 to 25, the first aperture 722 may include an angled inner surface 750 permitting receipt of endoscopes 714 of various sizes. Such an embodiment would be particularly useful when employed in conjunction with the embodiment disclosed with reference to FIGS. 11 to 13. As such, the center tab may be torn away to reduce hoop stresses and allow for insertion of larger diameter endoscopes. In addition to tearing the center tab, additional tabs may be torn away until a desired holding force is achieved.

As those skilled in the art will certainly appreciate, the present invention has application in conventional endoscopic and open surgical instrumentation as well application in robotic-assisted surgery. Preferably, the invention described herein will be processed before surgery. First, a new, or used, attachment apparatus is obtained and, if necessary, cleaned. The attachment apparatus can then be sterilized. In one sterilization technique, the attachment apparatus is placed in a closed and sealed container, such as a plastic of TYVEK bag. The container and attachment apparatus are then placed in a field of radiation that can penetrate the container, such as gamma radiation, x-rays, or high-energy electrons. The radiation kills bacteria on the attachment apparatus and in the container. The sterilized attachment apparatus can then be stored in the sterile container. The sealed container keeps the attachment apparatus sterile until it is opened in the medical facility. As those skilled in the art will appreciate, sterilization may be achieved in any number of ways known to those skilled in the art including beta or gamma radiation, ethylene oxide, steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An endoscopic attachment apparatus for coupling an endoscope with an endoscopic instrument, comprising:
   an attachment ring including a ring body having first and second apertures respectively shaped and dimensioned for the receipt of an endoscope and an endoscopic instrument;
   wherein the attachment ring includes an annular body defining the first aperture and the annular body is provided with an endoscope release mechanism for facilitating release of the endoscope from the attachment ring, wherein the release mechanism include a tear strip formed along the annular body the tear strip including a tab at an end thereof for engagement by a medical practitioner.

2. The endoscopic attachment apparatus according to claim 1, wherein the tear strip includes first and second slots molded along the annular body.

3. The endoscopic attachment apparatus according to claim 2, wherein the tear strip is provided with a tear tab at its free first end.

4. The endoscopic attachment apparatus according to claim 1, further including a tube installed in the second aperture, the tube extending proximally from the second aperture in a manner defining a passageway for the introduction of the endoscopic instrument to a surgical site without the removal of the endoscope.

5. The endoscopic attachment apparatus according to claim 1, wherein the release mechanism includes a helical tear away mechanism.

6. The endoscopic attachment apparatus according to claim 5, wherein the helical tear away mechanism includes a helically oriented thick area and a helically oriented thin area oriented in a manner permitting ripping of the annular body.

7. The endoscopic attachment apparatus according to claim 6, wherein the helical tear away mechanism includes first and second tabs at opposite ends of the tear strip secured to the thick area such that when the tab is pulled in a lateral manner the thin area is ripped such that a tear propagates from the tab helically along a longitudinal extent of the annular body.

8. The endoscopic attachment apparatus according to claim 1, wherein the release mechanism includes a series of tear strips defined by radically oriented thick areas and thin areas.

9. The endoscopic attachment apparatus according to claim 8, further including tabs secured to the respective thick areas.

10. The endoscopic attachment apparatus according to claim 1, wherein the release mechanism includes an insert providing a guide for cutting of the annular body in a manner permitting release of the endoscope therefrom.

11. The endoscopic attachment apparatus according to claim 1, wherein the release mechanism includes an insert formed of a brittle material.

12. The endoscopic attachment apparatus according to claim 11, wherein the insert forms part of the annular body permitting cracking of the insert for opening of the annular body.

13. The endoscopic attachment apparatus according to claim 1, wherein the first aperture is shaped and dimensioned for frictional engagement with an outer surface of the endoscope in a manner preventing rotation of the attachment ring relative to the endoscope.

14. The endoscopic attachment apparatus according to claim 1, wherein the second aperture is slightly larger than a shaft of the endoscopic instrument in a manner permitting movement of the endoscopic instrument relative to the endoscope for improved access to tissue.

15. The endoscopic attachment apparatus according to claim 1, wherein the ring body includes a first member and a second member defining the first aperture there between, wherein the first member and the second member are releasably secured in a manner defining the release mechanism permitting selective release of an endoscope from within the first aperture.

16. The endoscopic attachment apparatus according to claim 15, wherein the first member is substantially cylindrical and includes first and second outwardly extending flanges at free edges thereof, the first and second outwardly extending flanges being shaped and dimensioned for engaging the second member in a manner securely attaching the present attachment apparatus about an endoscope.

17. The endoscopic attachment apparatus according to claim 16, wherein the second member is a substantially elongated member shaped and dimensioned for engagement with the first and second flanges of the first member in a manner connecting the first and second edges of the first member to close a central aperture defined thereby.

18. The endoscopic attachment apparatus according to claim 15, further including an instrument ring defining the second aperture.

19. The endoscopic attachment apparatus according to claim 18, wherein the instrument is pivotally secured to the first member allowing the instrument ring to pivot relative to the first aperture.

* * * * *